(12) United States Patent
Puchhammer

(10) Patent No.: US 7,867,287 B2
(45) Date of Patent: *Jan. 11, 2011

(54) HAND PROSTHESIS WITH FINGERS THAT CAN BE ALIGNED IN AN ARTICULATED MANNER

(75) Inventor: Gregor Puchhammer, Vienna (AT)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/097,804

(22) PCT Filed: Dec. 7, 2006

(86) PCT No.: PCT/DE2006/002177

§ 371 (c)(1),
(2), (4) Date: Jun. 17, 2008

(87) PCT Pub. No.: WO2007/076765

PCT Pub. Date: Jul. 12, 2007

(65) Prior Publication Data

US 2008/0262636 A1    Oct. 23, 2008

(30) Foreign Application Priority Data

Dec. 20, 2005   (DE) .................. 10 2005 061 313

(51) Int. Cl.
*A61F 2/54*  (2006.01)
*A61F 2/68*  (2006.01)

(52) U.S. Cl. .................. 623/64; 623/57; 623/24

(58) Field of Classification Search .................. 623/57, 623/63–65, 24; 901/30, 32, 36, 38
See application file for complete search history.

(56) References Cited

U.S. PATENT DOCUMENTS

| 1,225,415 | A | * | 5/1917 | Cronemiller .................. 623/58 |
| 1,630,277 | A | | 5/1927 | Smith |
| 2,433,301 | A | | 12/1947 | Simpson |
| 2,553,827 | A | | 5/1951 | Mason |
| 2,859,450 | A | | 11/1958 | Becker |
| 3,026,534 | A | | 3/1962 | Brown |
| 4,114,464 | A | | 9/1978 | Schubert et al. |
| 4,149,278 | A | | 4/1979 | Frosch et al. |

(Continued)

FOREIGN PATENT DOCUMENTS

DE    19854762    6/2000

(Continued)

OTHER PUBLICATIONS

International Search Report for PCT/DE2006/002177, 3 pgs., mailed Aug. 3, 2007.

(Continued)

*Primary Examiner*—William H Matthews
*Assistant Examiner*—Marcia Hoffman
(74) *Attorney, Agent, or Firm*—Holland & Hart, LLP

(57) ABSTRACT

A hand prosthesis includes a chassis to which a number of finger prostheses are articulated. Each of the finger prostheses are movable relative to the chassis and toward one another about at least one swiveling axis via a drive that is connected to the finger prostheses by a force transmission unit.

17 Claims, 6 Drawing Sheets

U.S. PATENT DOCUMENTS

| | | | |
|---|---|---|---|
| 4,246,661 A | 1/1981 | Pinson | |
| 4,364,593 A | 12/1982 | Maeda | |
| 4,623,354 A | 11/1986 | Childress et al. | |
| 4,643,473 A * | 2/1987 | Douglas | 294/111 |
| 4,685,924 A | 8/1987 | Massey | |
| 4,685,929 A | 8/1987 | Monestier | |
| 4,792,338 A * | 12/1988 | Rennerfelt | 623/64 |
| 4,921,293 A | 5/1990 | Ruoff et al. | |
| 4,955,918 A | 9/1990 | Lee | |
| 5,080,682 A | 1/1992 | Schectman | |
| 5,888,246 A | 3/1999 | Gow | |
| 6,660,043 B2 | 12/2003 | Kajitani et al. | |
| 6,896,704 B1 * | 5/2005 | Higuchi et al. | 623/64 |
| 2003/0195638 A1 | 10/2003 | Kajitani et al. | |
| 2004/0015240 A1 | 1/2004 | Archer et al. | |
| 2005/0021154 A1 | 1/2005 | Brimalm | |

FOREIGN PATENT DOCUMENTS

| | | |
|---|---|---|
| DE | 19906294 | 9/2000 |
| DE | 20301116 | 3/2003 |
| DE | 10237373 | 3/2004 |
| EP | 0045818 | 2/1982 |
| EP | 0219478 | 10/1986 |
| EP | 1195151 | 4/2002 |
| FR | 2236478 | 2/1975 |
| GB | 1175830 | 12/1966 |
| GB | 1201182 | 8/1967 |
| GB | 1585256 | 6/1976 |
| GB | 1571140 | 11/1977 |
| WO | 03017880 | 3/2003 |
| WO | WO 03/017876 | 3/2003 |

OTHER PUBLICATIONS

International Search Report and Written Opinion issued in PCT/DE2006/002175, 8 pages, mailed Aug. 3, 2007.

International Search Report and Written Opinion issued in PCT/DE2006/002176, 9 pages, mailed Aug. 3, 2007.

Non-Final Office Action mailed Aug. 21, 2009 for U.S. Appl. No. 12/097,800, 14 pages.

Non-Final Office Action mailed Aug. 24, 2009 for U.S. Appl. No. 12/097,798, 14 pages.

* cited by examiner

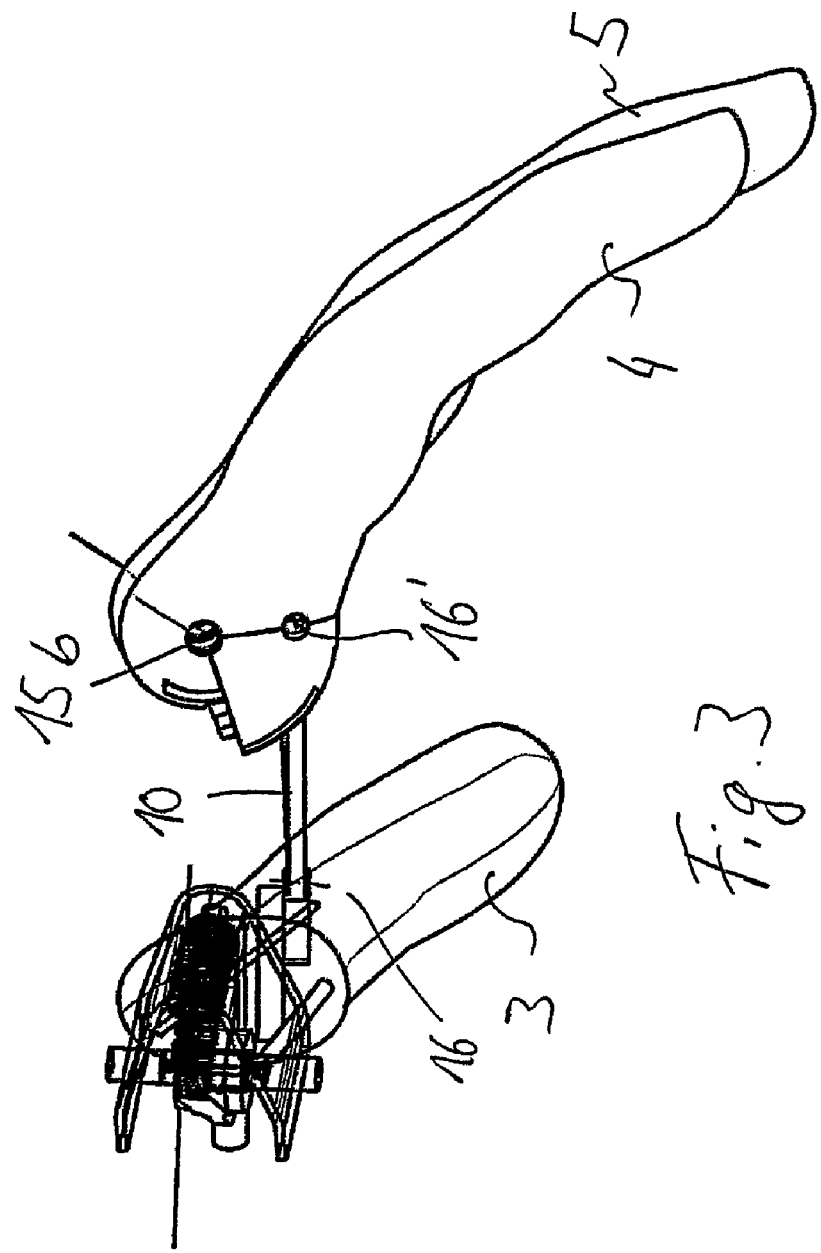

HAND PROSTHESIS WITH FINGERS THAT CAN BE ALIGNED IN AN ARTICULATED MANNER

CROSS-REFERENCE TO RELATED APPLICATION

This application is a national phase application, filed pursuant to 35 U.S.C. §371, of PCT/DE2006/002177 filed Dec. 7, 2006, and claims priority to DE 10 2005 061 313.6 filed Dec. 20, 2005, which are herein incorporated by reference in their entirety.

TECHNICAL FIELD

The invention relates to a hand prosthesis comprising a chassis, to which a number of finger prostheses are articulated, said finger prostheses being movable relative to the chassis and toward one another about at least one swiveling axis by means of a drive.

BACKGROUND

An object of a hand prosthesis is to reproduce as accurately as possible the appearance and the function of a hand that has had to be replaced. For this purpose, the hand prosthesis should include gripping devices, which may be formed as replicas of fingers, in relation to one another, in order to allow gripping of an object.

US 2003/00195638 A1 discloses a two-finger gripper in which two gripping devices can be displaced from an open position into a closed position, and in which the gripping devices lie directly opposite each other. In this way, an object located between the gripping devices can be held. To release the grip, a reversal of the direction of rotation of the drive can be initiated.

WO 03/017880 A1 discloses a prosthetic hand in which a separate drive is arranged in each individual finger prosthesis, which is mounted on a chassis. With such a prosthetic hand, it is possible to realize different gripping situations, for example fingertip gripping or lateral gripping. Disadvantages are the high degree of control required for each individual finger, the complex technology, with drives integrated in the finger, and increased susceptibility to faults on account of the complex type of construction.

SUMMARY

An object of the invention is to provide a hand prosthesis which has simple control, operates reliably and can be produced at low cost.

In one embodiment, the hand prosthesis according to the invention, comprises a chassis, to which a number of finger prostheses are articulated. The finger prostheses are each movable relative to the chassis about at least one swiveling axis by means of a drive, which is connected to the finger prosthesis by means of force transmission unit. The force transmission units are on a common drive and are coupled to the finger prostheses in such a way that, starting from a rest position of the finger prostheses, at least two finger prostheses go through different adjusting angles relative to the chassis depending on the direction of rotation of the drive. If the drive is activated in one direction of rotation, for example, first the index finger and middle finger move from a rest position in the direction of the inner surface of the hand, while the thumb is activated later or more slowly. Then, so-called "lateral gripping" can be realized with these three fingers. In the case of the other direction of rotation, starting from the rest position, in which the hand prosthesis is held open, first the thumb is activated or moved more quickly in the direction of the inner surface of the hand, so that the tips of the finger prostheses are brought together, in order to realize "fingertip gripping". Therefore, a different time sequence of the movement takes place, depending on the direction of rotation of the drive. The finger prostheses are mechanically coupled to the drive, so that it is possible with a low degree of control, by a simple reversal of the direction of rotation, to set two different gripping states with which the most frequent gripping tasks can be performed.

Apart from the different adjusting angles, which provide either fingertip gripping or lateral gripping, different fingertip gripping positions can also be provided by making the mechanism appropriately match desired requirements. The mechanical coupling can be produced at very low cost. In addition, only a single, common drive is required, preferably accommodated or housed in the chassis of the prosthetic hand The drive can be made much more efficiently in its design on account of the generous space provided in the chassis, in comparison with the space available in the finger prostheses.

In one embodiment, the force transmission units are rotatably mounted on a swiveling coupling element, for example a rotary disk, to transmit the desired forces with minimal incidental forces that result from instances of material bending in the case of rigid mounting. The coupling element may itself be formed in a rotatable or swiveling manner. In one configuration, a rotary disk is arranged within the chassis such that the axis of rotation of the coupling element runs substantially orthogonal to the palmar surface of the chassis. A gear mechanism may be arranged between the drive and the coupling element to provide any required speed reduction. The output axis of the drive may lie orthogonal to the palmar surface of the chassis, so that any required gear stages can operate with parallel axes of rotation. Should a change in the direction of rotation or orientation of the axis of rotation be necessary on account of the geometry of the drive or the chassis, an angular gear mechanism may be utilized.

A novel and uncomplicated design for providing the different adjusting angles is achieved by couling the force transmission units to the coupling element in such a way that their mountings on the drive side have different dead center positions. By mounting a force transmission unit on a rotary disk, displacements occur in the course of the rotational movement of the rotary disk in the form of a sine curve. Depending on the angle of rotation covered, different displacements are brought about in a directional component. The rotatable mounting of the force transmission unit on the coupling element causes only the displacement in a directional component to be effective. The bearing points of the force transmission units on the coupling element or the rotary disk are chosen such that, when activation takes place in the first direction of rotation, first the thumb goes through a dead center position, then the other prosthetic fingers, for example the index finger and the middle finger, are displaced. In the opposite direction of rotation, the adjusting path for the index finger and middle finger is smaller than that for the thumb.

Alternatively, different adjusting angles may be realized by a force transmission unit rolling on a cam disk, the radius of which is different for each direction of rotation. If, starting from a rest position, the cam disk is moved in the first direction of rotation, the force transmission units, for example in the form of tension belts, are rolled onto a cam disk with a greater radius than the force transmission unit for the thumb. As a result, first the index finger and middle finger are displaced in the palmar direction, while the thumb follows. In the opposite direction of rotation, this takes place correspondingly in the reverse sense. A return movement can be performed by means of spring biasing of the finger prostheses. The cam disks also allow different movement sequences of the individual finger prostheses to be set, for example first a high swiveling speed that decreases with an increasing swiveling angle of the finger prostheses, or vice versa.

To be able to transmit high forces, the drive may be as a pancake motor that is positioned in the chassis, which may be configured in the form of the metacarpus. The pancake motor, which may be formed as a slow-running motor, can produce high torques with a relatively compact construction and low rotational speeds. The rotational speeds may be reduced further to the desired speed by means of a cycloidal gear mechanism or a harmonic-drive gear mechanism.

In one embodiment, the force transmission units are formed so as to be rigid under tension and yielding under pressure or elastic under bending. As such, limited elasticity is possible with palmar force transmission to the finger prostheses, while opening the prosthetic hand is not possible without unlocking the drive or reversing the direction of rotation. As a result, secure gripping is ensured. The force transmission units may, to a certain extent, be stable under pressure to provide compressive forces to assist an opening movement.

For the stable transmission of tensile forces, the force transmission component may have a cable, stranded-wire or fiber component (collectively referred to herein as the cable component).

The cable component may be formed as an open, closed or twisted loop and have an elastomer component to make displacement on all sides possible, for example in the case of incorrect axial positions. Furthermore, the elastomer component protects the cable component from external influences if it at least partially encloses the cable component.

Bearing bushings for receiving axial spindles that are associated with the chassis or drive and the finger prostheses may be located in the force transmission unit. With a resiliently elastic configuration of the force transmission units, spring rates may be set such that, when the force transmission unit is subjected to the force of a pressure, a return of the finger prosthesis into a starting position occurs.

BRIEF DESCRIPTION OF THE DRAWINGS

An exemplary embodiment of the invention is explained in more detail below on the basis of the accompanying figures, in which:

FIG. 3 shows a side view of FIG. 2;

DETAILED DESCRIPTION

Figure 1:
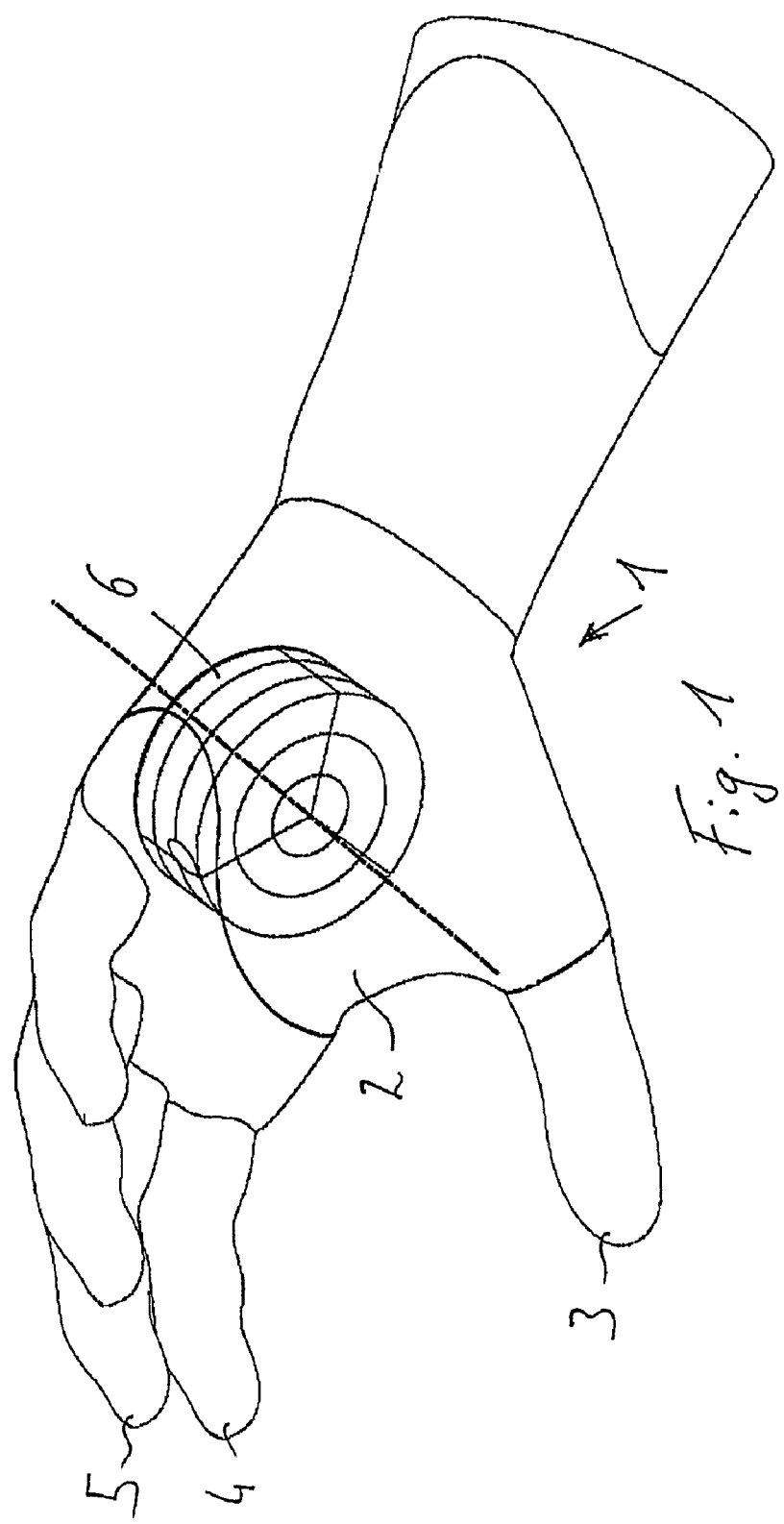
FIG. 1 shows a schematic representation of a hand prosthesis.

FIG. 1 shows a hand prosthesis 1, comprising a hand chassis 2 and at least three finger prostheses 3, 4, 5 articulated to the hand chassis 2. The finger prostheses 3, 4, 5 correspond to the thumb, index finger and middle finger, respectively, of a natural hand. Movable mounting of these three finger prostheses 3, 4, 5, which can be actuated by means of a common drive 6, allows a plurality of gripping tasks of a hand to be performed. The two other fingers, the ring finger and the small finger, can be passively moved along with the other fingers and consist of an elastomer material, to achieve an appearance that looks as natural as possible. The drive 6 is mounted within the hand chassis 2 in the form of an electric motor with an associated gear mechanism (as shown in other figures). A power source for the drive 6 (not shown or represented), may likewise be located within the hand chassis 2. The drive 6 is activated by means of a control device (also not shown), which may be located in the hand chassis 2. The corresponding signals may be generated by means of a remote control or take the form of myoelectrical signals.

Figure 2:
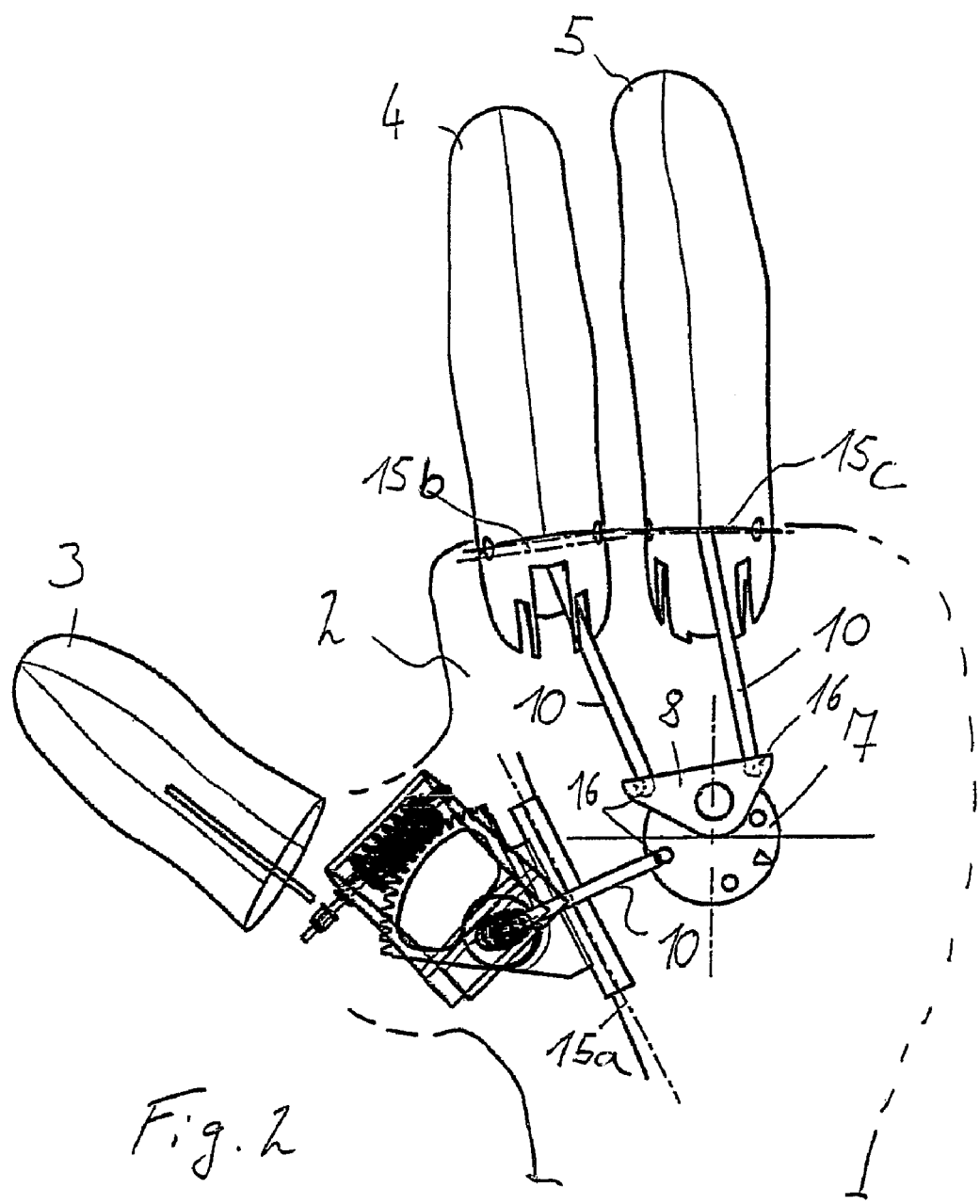
FIG. 2 shows a schematic representation of the functional setup of a hand prosthesis in a palmar plan view.

FIG. 2 is a schematic representation of the functional mode of the hand prosthesis 1. The three finger prostheses 3, 4, 5 are mounted on the hand chassis 2 such that they can swivel about articulating axes 15*a-c*. The finger prostheses 3, 4, 5 are connected via force transmission units 10, (the construction of which is described in detail further below), to a rotary disk 7, which is driven by the electric motor drive 6. The force transmission units 10 are mounted to the rotary disk 7 on spindles 16, either directly or by way of a rocker 8. The index finger 4 and the middle finger 5 are coupled to each other by way of the rocker 8, which is rotatably mounted on the rotary disk 7. The rotary disk 7 itself is mounted either directly on an output shaft of the drive 6 or on an output shaft of a gear-mechanism mounted to the drive 6.

If the drive 6 is activated, the rotary disk 7 is moved a corresponding rotational angle. As a result, the spindles 16 are displaced in relation to the swiveling axes 15*a-c* of the finger prostheses 3, 4, 5, which leads to a swiveling of the finger prostheses 3, 4, 5. This is due to the tensionally rigid formation of the force transmission units 10 and an articulation of the force transmission units 10 on the finger prostheses 3, 4, 5 that is at a distance from the axes of rotation 15*a-c*. If the drive 6 is reversed and the rotary disk 7 moves into a position in which the spindles 16 are at a minimal distance from the swiveling axes 15*a-c* of the finger prostheses 3, 4, 5, the opened starting position of the rotary disk 7 and drive 6 is reached. The finger prostheses 3, 4, 5 then move into their opened starting position, as a result of the resiliently elastic properties of the force transmission units 10. It is provided here that the force transmission units 10 can transmit much higher tensile forces than compressive forces. This corresponds to the physiological conditions of a natural hand, which can apply much greater forces when closing the hand than when opening it. For reasons of overall clarity, the ring finger and the small finger are not represented; they can be passively articulated to the middle finger 5 and thereby moved along with it. It is also possible for the ring finger and the small finger to be articulated on the widened rocker 8, to which further force transmission units 10, actively articulating further finger prostheses 3, 4, 5, are coupled.

Figure 4A:
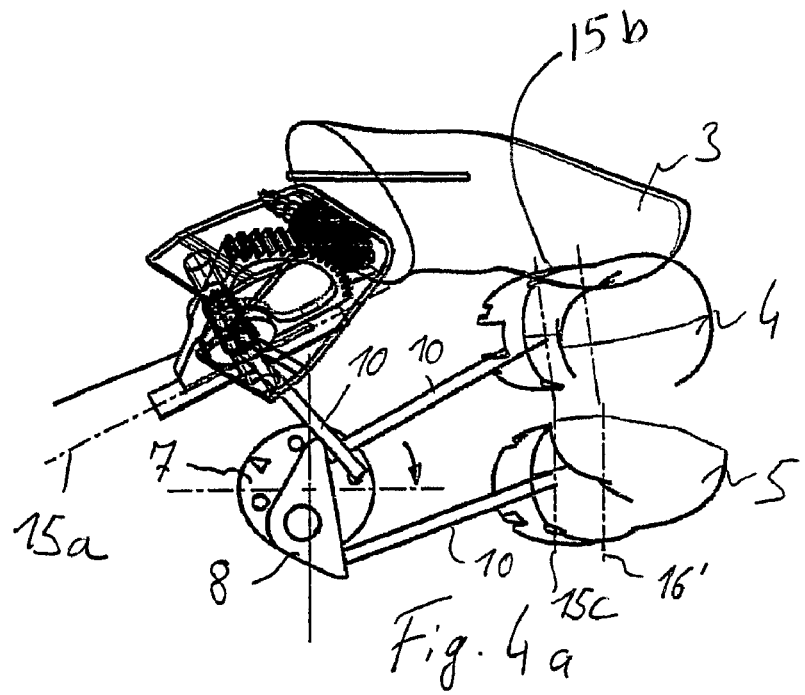
FIGS. 4*a-b* show a closed hand in the act of lateral gripping.
Figure 4B:
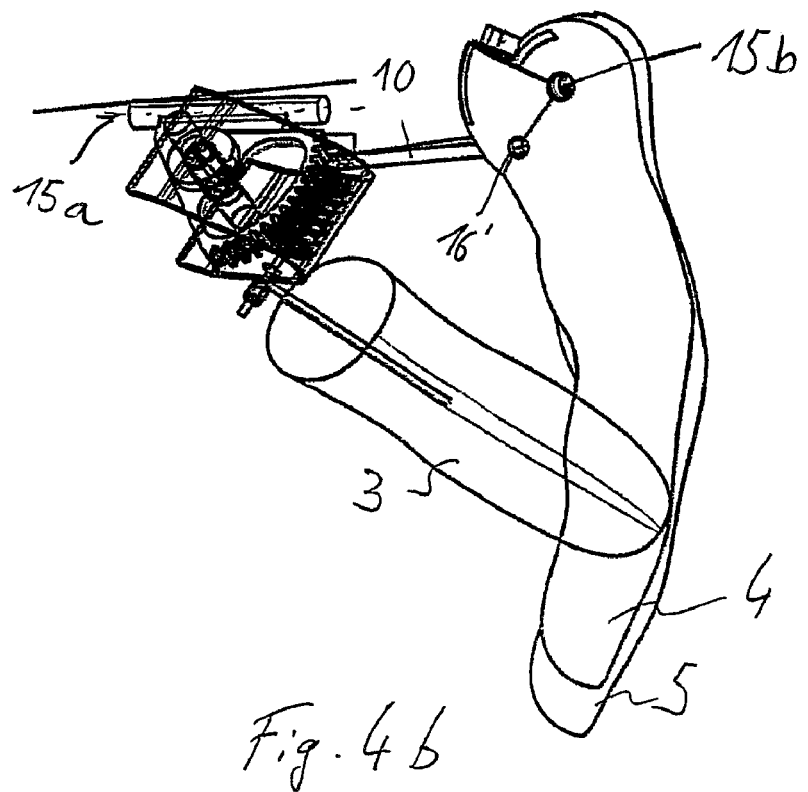

FIG. 3 is a side view of FIG. 2, with the hand prosthesis 1 in a rest position and the thumb 3, the index finger 4 and the middle finger 5 represented in a slightly opened position of rest, approximating the position in which the hand is naturally held. It can be seen from this figure that the force transmission units 10 are articulated to the finger prostheses 4, 5 at bearing points 16', which are at a distance from the axes of rotation 15*b-c* of the finger prostheses 4, 5. Bending of the finger prostheses 4, 5 is brought about by a displacement of the spindle 16 on the coupling element 7, as a result of the transmitted tensile forces. Starting from the rest position shown in FIGS. 2 and 3, when the rotary disk 7 is turned in the clockwise sense, as shown in FIG. 4*a*, first the index-finger and middle-finger prostheses 4, 5 move in the direction of the inner surface of the hand. The thumb prosthesis 3 is only displaced thereafter in the direction of the inner surface of the hand, since the force transmission unit 10 that is assigned to the thumb prosthesis 3 first has to go through the dead center, which is the shortest distance between the spindle 16 on the drive side and the swiveling axis 15a. The particular arrangement of the force transmission units 10 of the index-finger and middle-finger prostheses 4, 5 results in displacement in the palmar direction more quickly, or over a wider angular range, so that the thumb prosthesis 3 bears against the radial side of the index-finger prosthesis 4. As a result, lateral gripping is possible.

Figure 5A:
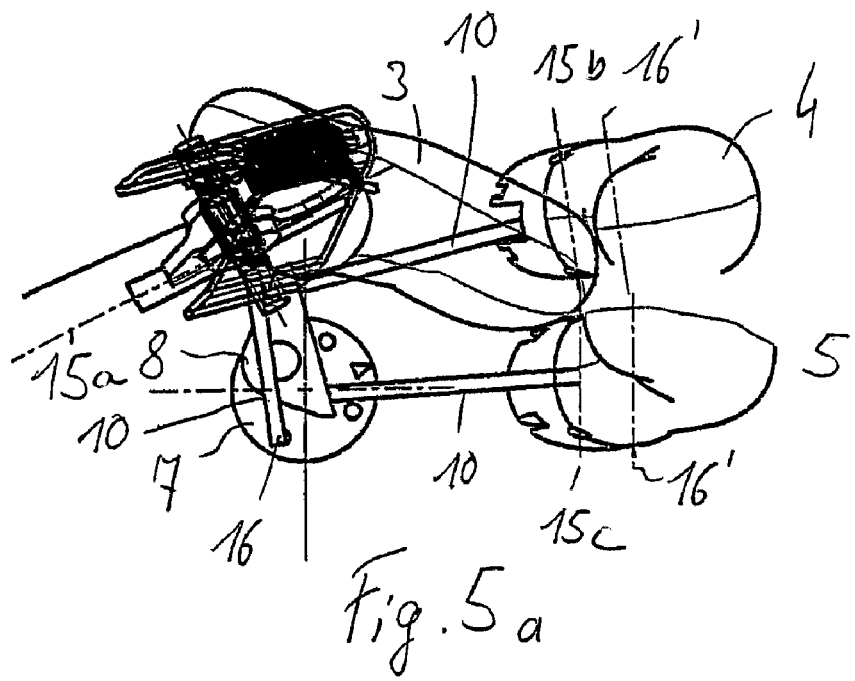
FIG. 5*a-b* show a closed hand in the act of fingertip gripping.
Figure 5B:
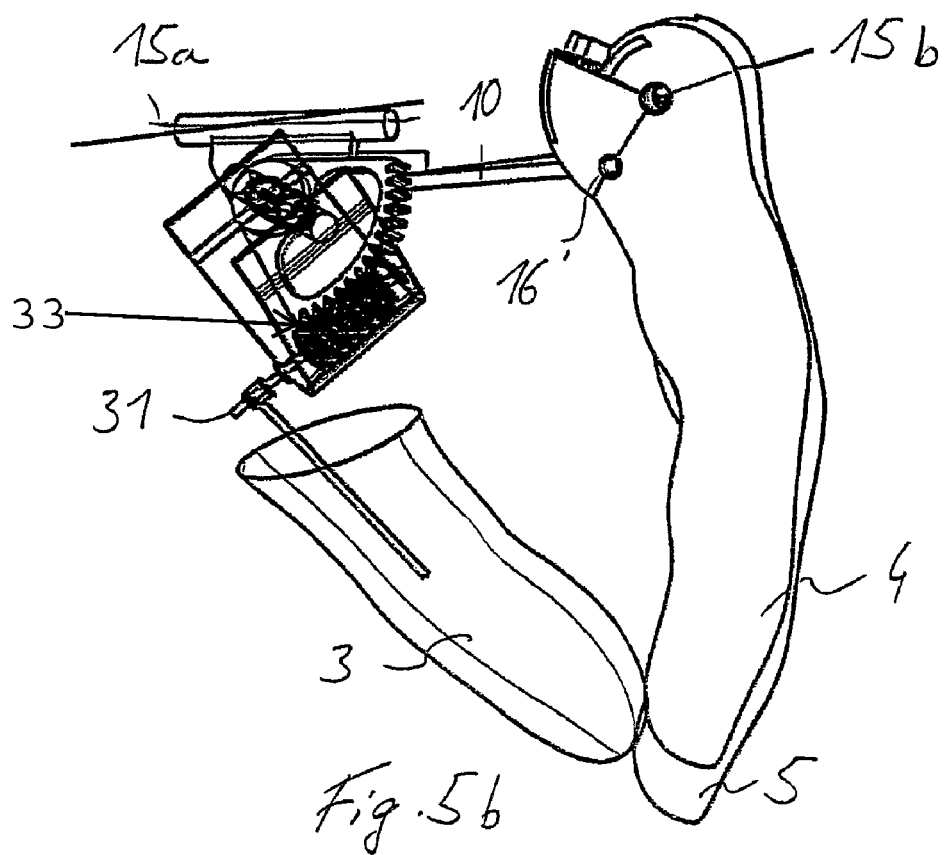

FIGS. 5a-b is the position of the finger prostheses 3, 4, 5 in the case of a direction of rotation in the counterclockwise sense. The thumb prosthesis 3 is first moved in the palmar and ulnar directions about the swiveling axis 15a, while the finger prostheses 4, 5 first go through their dead center, or are articulated to the rotary disk 7 in such a way that only a small angular displacement is realized for a corresponding rotational angle. Therefore, the thumb prosthesis 3 is first guided inward and the tips of the finger prostheses 3, 4, 5 lie against one another in their end positions, so that fingertip gripping is accomplished.

Figure 6:
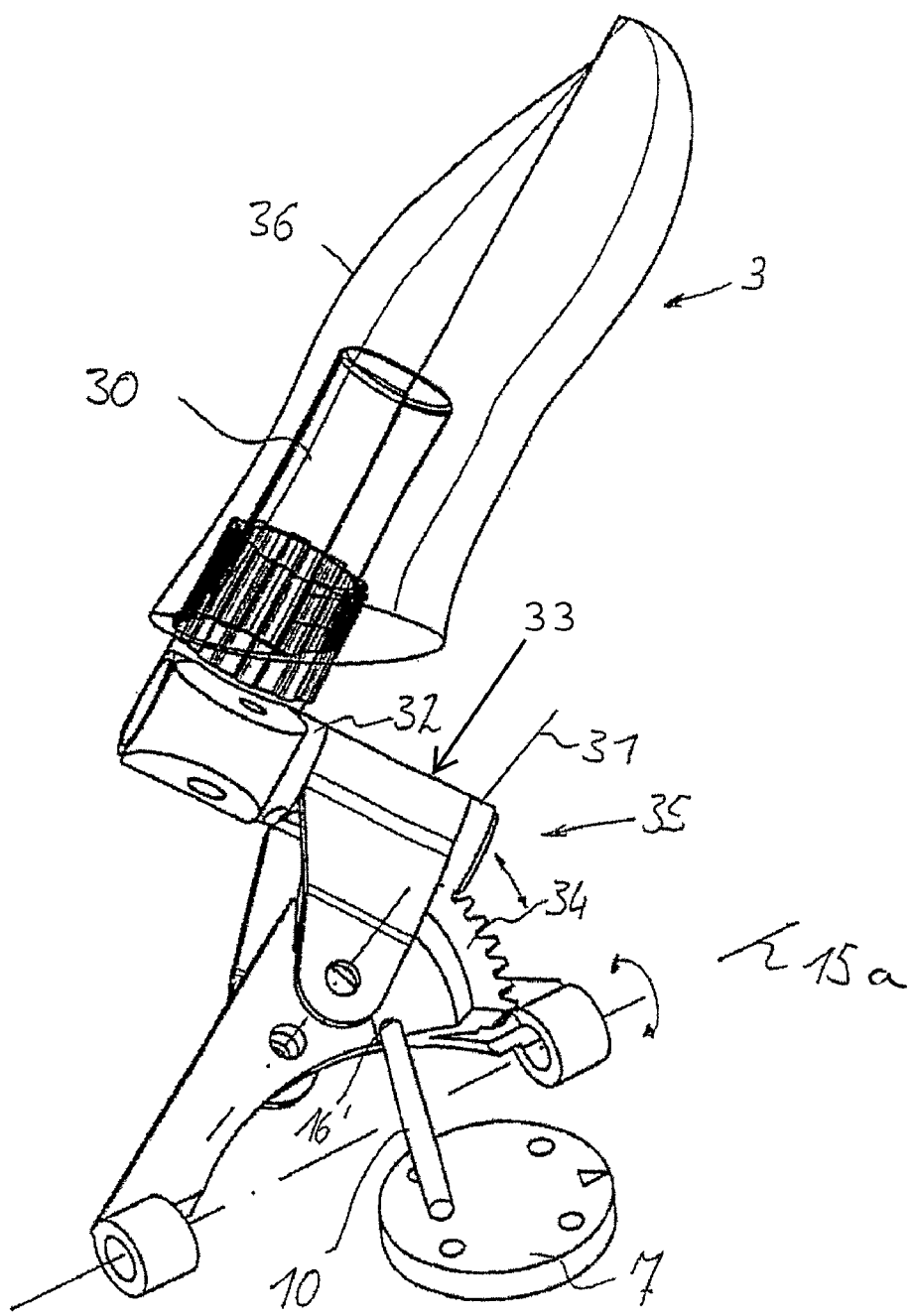
FIG. 6 shows an individual representation of a thumb prosthesis.

To provide additional gripping possibilities, an additional drive may be provided in the thumb prosthesis 3, as shown in FIG. 6. In FIG. 6, it can also be seen that, apart from the first swiveling axis 15a, the thumb prosthesis 3 has a second swiveling axis 31 (coming out of the page at an angle), about which at least the distal end of the thumb prosthesis 3 is swivel-mounted. A second drive 30 and an inclined-screw gear mechanism 32 or a multiple-threaded worm gear mechanism are used to move an output worm 33. The worm 33 meshes with a gearwheel segment 34 and so brings about a displacement of the finger prosthesis 3, including the drive 30 and the gear mechanism 32, about the swiveling axis 31. If both drives 6, 30 are activated at the same time, a combined movement of the thumb prosthesis 3 in the palmar and ulnar directions is performed in accordance with the displacement speeds, which corresponds to the natural mobility of a thumb.

FIG. 6 shows the function of the thumb prosthesis 3 in detail, including a molding 36, which replicates the contour of a natural thumb. Inside the molding 36, which is formed as a hollow body, there is a free space in which the second drive 30 is located and fastened. The molding 36 is consequently coupled, for example adhesively attached, firmly clamped, or positively connected to the drive 30. The drive 30 is coupled to the gearwheel segment 34 by means of an angular gear mechanism in the form of an inclined-screw gear mechanism 32 and the worm 33.

Upon activating the drive 30, the worm 33 is turned in one direction or the other. As a result of the swivel-mounting about the axis of rotation 31 on the gearwheel segment 34, a movement about the swiveling axis 31 is possible in the direction of the double-headed arrow. A radial or ulnar movement may thereby be performed. The gearwheel segment 34 itself is swivel-mounted about the first swiveling axis 15a and can be swiveled in a palmar or dorsal direction by a turning of the rotary disk 7 and the corresponding displacement of the force transmission element 10. This swiveling movement is likewise indicated by the double-headed arrow around the swiveling axis 15a.

The second drive 30 is likewise an electric motor and may be located along the longitudinal axis between what would be the carpometacarpal joint and the interphalangeal joint. As a result of the small type of construction and the possible need for high drive torque, the drive 30 may be formed as a fast-running motor. The speed-transforming gear mechanism 32 is formed as an inclined-screw gear mechanism producing deflections of the drive axis in relation to the longitudinal axis of the second drive 30 in an angular range of 45° to 135°. By angling away the output spindle the worm 33, which meshes with the gearwheel segment 34, brings about a corresponding movement of the thumb.

The first drive 6, arranged in the hand chassis 2, is a slow-running pancake motor with a high torque, which is coupled to a highly speed-reducing gear mechanism 32, to allow a correspondingly slow and forceful gripping movement to be performed. The control signals may either be generated by a remote control or be myoelectrical signals and have a control device. By means of this first drive 6 and the rotary disk 7, it is possible to displace the gearwheel segment 34 together with the worm 33, as well as the gear mechanism 32 and the drive 30 covered by the molding 36.

The invention claimed is:

1. A hand prosthesis comprising:
a chassis including an inner palmar surface;
a plurality of finger prostheses articulated or elastically coupled to the chassis;
a single motorized drive coupled to the plurality of finger prostheses, the drive configured to rotate in a first direction and a second direction to articulate each of the plurality of finger prostheses about a swiveling axis relative to the chassis from a rest position toward the inner palmar surface; and
a plurality of force transmission units, each unit coupling one of the plurality of finger prostheses to the motorized drive,
wherein upon rotation of the motorized drive in the first direction at least two of the plurality of finger prostheses articulate about the swiveling axis to a first gripping position defined by a first adjustment angle of each articulated finger; and
wherein upon rotation of the motorized drive in a second direction the at least two finger prostheses articulate about the swiveling axis to a second gripping position defined by a second and different adjustment angle of each articulated finger.

2. The hand prosthesis as claimed in claim 1, further comprising a coupling element having an axis of rotation about which the coupling element swivels, and wherein the plurality of force transmission units are rotatably mounted on the coupling element.

3. The hand prosthesis as claimed in claim 2, wherein the coupling element is a rotary disk.

4. The hand prosthesis as claimed in claim 2 wherein the axis of rotation of the coupling element is aligned substantially orthogonal to the inner palmar surface of the chassis.

5. The hand prosthesis as claimed in claim 2, wherein the plurality of force transmission units are each coupled to the coupling element such that each force transmission unit's drive side mounting has a different dead center position.

6. The hand prosthesis as claimed in claim 2, further comprising a cycloidal gear mechanism or a harmonic-drive gear mechanism on which the coupling element is located.

7. The hand prosthesis as claimed in claim 1, wherein an output axis of the drive is aligned substantially orthogonal to the inner palmar surface of the chassis.

8. The hand prosthesis as claimed in claim 1, wherein the drive comprises a pancake motor.

9. The hand prosthesis as claimed in claim 1, wherein each force transmission unit is rigid under tension and yielding under pressure or elastic under bending.

10. The hand prosthesis as claimed in claim 1, wherein each force transmission unit comprises a cable, stranded-wire or fiber component.

11. The hand prosthesis as claimed in claim 10, wherein the cable, stranded-wire or fiber component is a closed loop.

12. The hand prosthesis as claimed in claim 10, wherein each force transmission unit comprises an elastomer component.

13. The hand prosthesis as claimed in claim 12, wherein the elastomer component at least partially encloses the cable, stranded-wire or fiber component.

14. The hand prosthesis as claimed in claim 1, wherein each force transmission unit comprises an elastomer component.

15. The hand prosthesis as claimed in claim 1, wherein the force transmission units comprise bearing bushings for receiving axial spindles that are provided by the chassis and the finger prostheses, with the chassis spindles directly or indirectly mounted to the drive and the finger prostheses spindles mounted within the finger prostheses.

16. The hand prosthesis as claimed in claim 1, wherein each force transmission unit is formed in a resiliently elastic manner.

17. The hand prosthesis as claimed in claim 16, wherein a spring rate of each force transmission unit is set to return a finger prosthesis into a starting position when each force transmission unit is subjected to a force due to pressure applied to the finger prosthesis.

* * * * *